US007037329B2

(12) United States Patent
Martin

(10) Patent No.: US 7,037,329 B2
(45) Date of Patent: May 2, 2006

(54) BIFURCATED STENT FOR PERCUTANEOUS ARTERIALIZATION OF THE CORONARY SINUS AND RETROGRADE PERFUSION OF THE MYOCARDIUM

(75) Inventor: Eric C. Martin, 134 Old Post Rd. North, Croton On Hudson, NY (US) 10520

(73) Assignee: Eric C. Martin, Croton On Hudson, NY (US)

( * ) Notice: Subject to any disclaimer, the term of this patent is extended or adjusted under 35 U.S.C. 154(b) by 480 days.

(21) Appl. No.: 10/036,445

(22) Filed: Jan. 7, 2002

(65) Prior Publication Data

US 2003/0130719 A1 Jul. 10, 2003

(51) Int. Cl.
*A61F 2/06* (2006.01)

(52) U.S. Cl. .......................................... 623/1.13; 604/8

(58) Field of Classification Search ............... 623/1.12, 623/1.15, 1.35, 1.13; 604/8
See application file for complete search history.

(56) References Cited

U.S. PATENT DOCUMENTS

| 2,127,903 A | 8/1938 | Bowen |
| 5,180,392 A | 1/1993 | Skeie et al. |
| 5,287,861 A | 2/1994 | Wilk |
| 5,380,316 A | 1/1995 | Aita et al. |
| 5,389,096 A | 2/1995 | Aita et al. |
| 5,409,019 A | 4/1995 | Wilk |
| 5,429,144 A | 7/1995 | Wilk |
| 5,549,581 A | 8/1996 | Lurie et al. |
| 5,653,743 A * | 8/1997 | Martin ................. 623/1.35 |
| 5,655,548 A | 8/1997 | Nelson et al. |
| 5,667,486 A | 9/1997 | Mikulich et al. |
| 5,755,682 A | 5/1998 | Knudson et al. |
| 5,824,071 A | 10/1998 | Nelson et al. |
| 5,897,588 A | 4/1999 | Hull et al. |
| 6,010,530 A | 1/2000 | Goicoechea |
| 6,015,432 A | 1/2000 | Rakos et al. |
| 6,017,365 A | 1/2000 | Von Oepen |
| 6,027,526 A | 2/2000 | Limon et al. |
| 6,053,942 A | 4/2000 | Eno et al. |
| 6,149,682 A * | 11/2000 | Frid ..................... 623/1.35 |
| 6,190,406 B1 | 2/2001 | Duerig et al. |
| 6,258,120 B1 | 7/2001 | McKenzie et al. |
| 6,371,981 B1 | 4/2002 | Yang et al. |
| 6,395,021 B1 | 5/2002 | Hart et al. |
| 6,562,066 B1 * | 5/2003 | Martin ................. 623/1.15 |
| 6,605,053 B1 | 8/2003 | Kamm et al. |

OTHER PUBLICATIONS

Gensini, G.G., et al., Anatomy of the Coronary Circulation in Living Man, Circulation, May 1965, pp. 778-784, vol. XXXI.
Eckstein, R.W., et al., Acute Effects of Elevation of Coronary Sinus Pressure, Circulation, Mar. 1953, pp. 422-436, vol. VII.

(Continued)

*Primary Examiner*—(Jackie) Tan-Uyen T. Ho
(74) *Attorney, Agent, or Firm*—Milbank, Tweed, Hadley & McCloy LLP

(57) ABSTRACT

The present invention provides a novel bifurcated stent for providing retrograde flow of oxygenated blood from the left ventricle to the myocardium via the coronary sinus without a significant or deleterious left-to-right shunt. The present invention includes a main covered stent and a side limb, generally contemplating a Y or a T shaped bifurcated stent.

129 Claims, 6 Drawing Sheets

OTHER PUBLICATIONS

Gardner, R.S., et al., Arterialization of Coronary Veins in the Treatment of Myocardial Ischemia, The Journal of Thoracic and Cardiovascular Surgery, Aug. 1974, pp. 273-282, vol. 68, No. 2.

Zajtchuk, R., et al., Revascularization of the Heart through the Coronary Veins, The Annals of Thoracic Surgery, Apr. 1976, pp. 318-321, vol. 2, No. 4.

Patel, N.H., et al., Percutaneous Transmyocardial Intracardiac Retroperfusion Shunts: Technical Feasibility in a Canine Model, Journal of Vascular and Interventional Radiology, Mar. 2000, pp. 382-390, vol. 11, No. 3.

Rosch, J., et al., Coaxial Catheter-Needle System for Transjugular Portal Vein Entrance, Journal of Vascular and Interventional Radiology, Jan.-Feb. 1993, pp. 145-147, vol. 4.

Schofield, P.M., et al., Transmyocardial Laser Revascularisation in Patients with Refractory Angina: A Randomised Controlled Trial, The Lancet, Feb. 13, 1999, pp. 519-524, vol. 353.

Horvath, K.A., et al., Transmyocardial Laser Revascularization: Results of a Multicenter Trial with Transmyocardial Laser Revascularization Used as Sole Therapy for End-Stage Coronary Artery Disease, The Journal of Thoracic and Cardiovascular Surgery, Apr. 1997, pp. 645-653, vol., 113, No. 4.

Mohl, W., The Momentum of Coronary Sinus Interventions Clinically, Circulation, Jan. 1988, pp. 6-12, vol. 77, No. 1.

Mohl, W., The Relevance of Coronary Sinus Interventions in Cardiac Surgery, Thorac. Cardiovasc. Surgeon, 1991, pp., 245-250, vol. 39.

Kar, S., et al., Coronary Veins: An alternate Route to Ischemic Myocardium, Heart & Lung, Mar. 1992, pp. 148-157, vol. 21, No. 2.

Meerbaum, S., et al., Diastolic Retroperfusion of Acutely Ischemic Myocardium, The American Journal of Cardiology, Mar. 31, 1976, pp. 588-598, vol. 37.

Park, S.B., et al., Direct Selective Myocardial Revascularization by Internal Mammary Artery-Coronary Vein Anastomosis, The Journal of Thoracic and Cardiovascular Surgery, Jan. 1975, pp. 63-72, vol. 69, No. 1.

Hochberg, M.S., Selective Arterialization of the Coronary Venous System, The Journal of Thoracic and Cardiovascular Surgery, Jan. 1979, pp. 1-12, vol. 77, No. 1.

Chiu, C.J., et al., Selective Arterialization of Coronary Veins for Diffuse Coronary Occlusion, The Journal of Thoracic and Cardiovascular Surgery, Jul. 1975, pp., 177-182, vol. 70, No. 1.

Bhayana, J.N., et al., Reversal of Myocardial Ischemia by Arterialization of the Coronary Vein, Jan. 1974, pp. 125-132, vol. 67, No. 1.

Beck, C.S., et al., Scientific Basis for the Surgical Treatment of Coronary Artery Disease, Journal of American Medical Association, Nov. 26, 1955, pp. 1264-1971, vol. 159, No. 13.

Lazar, H.L., Coronary Sinus Interventions during Cardiac Surgery, The Annals of Thoracic Surgery, Oct. 1988, pp. 475-482, vol. 46, No. 4.

Moll, J.W., et al., Arterialization of the Coronary Veins in Diffuse Coronary Arteriosclerosis, J. Cardiovas. Surg., 1975, pp. 520-525., vol. 16.

Beck, C.S., Revascularization of the Heart, Surgery, Jul., 1949, pp. 82-88, vol. 26, No. 1.

Beck, C.S., et al., Operation for Coronary Artery Disease, Journal of American Medical Association, Dec. 29, 1951, pp. 1726-1731, vol. 147, No. 18.

Marco, J.D., et al., Coronary Venous Arterialization: Acute Hemodynamic, Metabolic, and Chronic Anatomical Observations, The Annals of Thoracic Surgery, May 1977, pp. 449-454, vol. 23, No. 5.

Beck, C.S., et al., Operations for Coronary Artery Disease, Journal of American Medical Association, Nov. 27, 1954, pp. 1226-1233, vol. 156, No. 13.

Eckstein, R.W., et al., Chronic Effects of Aorta-Coronary Sinus Anastomosis of Beck in Dogs, Circulation Research, Jan. 1954, pp. 60-72, vol. 11.

* cited by examiner

BIFURCATED STENT FOR PERCUTANEOUS ARTERIALIZATION OF THE CORONARY SINUS AND RETROGRADE PERFUSION OF THE MYOCARDIUM

BACKGROUND

I. Field of Invention

The present invention contemplates a bifurcated stent for supplying oxygenated blood retrogradely from the left ventricle to the myocardium through the coronary sinus. The percutaneously-delivered stent directs blood from the left ventricle to the coronary sinus. By controlling the amount of blood flowing into the bifurcated stent and the right atrium, blood is directed retrogradely through the side limb of the present invention to the heart tissue.

II. Description of Related Technology

Retrograde perfusion of the heart through the coronary sinus has long been known for treating end-stage heart disease. Previous methods, among others, have attempted to connect the aorta to the coronary sinus during open-heart surgery using a graft of the jugular vein, the internal mammary artery, or the carotid artery. Alternatively, an occlusion balloon has been used for a short period of time.

Nelson et al. (U.S. Pat. No. 5,824,071, 1998) discloses an apparatus and method for providing retrograde perfusion directly from the left ventricle to the coronary sinus. Although Nelson requires a pressure sensitive valve that prevents pressure build-up inside the coronary sinus from rising above 60 mm Hg, Nelson does not teach how such a valve may be constructed. Nelson does not teach or describe the features or components of such a pressure sensitive valve. Further, it is unlikely that such a device may be introduced percutaneously and will likely require invasive surgery.

In 2000, Patel et al. conducted an experiment for percutaneous arterialization of the coronary sinus using a stent. See Patel et al., *Percutaneous Transmyocardial Intracardiac Retroperfusion Shunts: Technical Feasibility in a Canine Model,* JVIR 2000, 11:382–390. The stent employed by Patel, et al., however, results in a significant shunting of oxygenated blood from the left ventricle to the right atrium (hereinafter "left-to-right shunt"). These shortcomings in the prior art are solved by the present invention.

SUMMARY OF INVENTION

The present invention incorporates by reference application Ser. No. 09/796,528, titled A STENT FOR ARTERIALIZATION OF CORONARY SINUS AND RETROGRADE PERFUSION OF THE MYOCARDIUM, filed Mar. 2, 2001, and application Ser. No. 10/036,441, TWO-PIECE STENT COMBINATION FOR PERCUTANEOUS ARTERIALIZATION OF THE CORONARY SINUS AND RETROGRADE PERFUSION OF THE MYOCARDIUM, filed Jan. 7, 2002.

It is an object of the present invention to provide a novel covered stent for providing retrograde flow of oxygenated blood from the left ventricle to the myocardium via the coronary sinus without a significant or deleterious left-to-right shunt. The present invention includes a main covered stent and a side limb, generally contemplating a Y or a T shaped bifurcated stent.

In a preferred embodiment, the bifurcated stent has a main covered stent and a side limb. The main covered stent preferably has a tubular shape with a passageway therethrough and has a leading end and a trailing end. The main covered stent preferably has a smaller cross-sectional area or passageway at the leading end and the trailing end in comparison to the remainder of the main covered stent. Also, the main covered stent has a main stent, which is covered with a graft. Optionally, the leading end portion of the main stent may not be covered. The main covered stent also has an opening about the middle portion of its length.

The side limb of the bifurcated stent is preferably either attached about the opening or fits within the opening to complete the T or Y shape. Thus, the side limb is in contact with the main covered stent about said opening. The side limb has a side stent and a cuff that is optional. The cuff, when present, is preferably attached to the graft of the main covered stent or is continuous with the main covered stent. A side stent, however, may or may not be attached (e.g., pre-attached or attached by being woven in a continuous manner to the main stent or by being stitched to the main stent) to the main stent. Thus, the side limb, which has a side stent and an optional cuff, provides a passageway for blood flow retrogradely to the myocardium.

Various embodiments are contemplated in the present invention. In one embodiment, the side limb may include both a cuff and a side stent, wherein the side stent is not attached to the main stent. In this embodiment, after the main covered stent is first delivered, the side stent is delivered to fit within the cuff. In another embodiment, the side limb may include the side stent but not the cuff, and the side stent is pre-attached to the main stent by being stitched or weaved (in a continuous fashion) to the main stent. In this embodiment, both the main covered stent and the side limb are delivered at the same time. In yet another embodiment, the side limb only has a side stent without the cuff, wherein the side stent is not attached to the main stent. In this embodiment, after the main covered stent is delivered, the side stent is delivered to fit within the opening.

For delivery, the main covered stent and the side limb may be compressed to fit within a catheter for percutaneous delivery into desired position. Upon delivery, the main covered stent may self expand to form a friction fit within the coronary sinus. The leading end is preferably positioned in the left ventricle, and the majority of the main covered stent fits substantially within the coronary sinus. The trailing end of the main covered stent may be in the right atrium or within the coronary sinus, preferably near the coronary ostium.

In delivering the present invention percutaneously, the opening or side limb is preferably aligned to face the upstream portion of the coronary sinus. All other lengths and placements preferably correlate to this placement. The side limb is positioned so that it preferably fits within the upstream portion of the coronary sinus and opens toward the myocardium. For fluoroscopic positioning, the opening is preferably marked with a ring made of radio-opaque material, such as platinum or gold.

Blood from the left ventricle flows through the leading end and into the main covered stent. Because of the graft, blood then flows either out into the right atrium through the trailing end or into the upstream portion of the coronary sinus through the opening and the side stent. Some blood may also flow back into the left ventricle. Thus, the size of the passageway at the leading end controls the amount of blood flowing into the main covered stent; the size of the passageway at the trailing end controls the amount of blood flowing into the right atrium ("left-to-right shunt"); and the size of passageway of the side limb controls the amount of blood flowing into the upstream portion of the coronary sinus. These three sizes are interrelated, and therefore interdependently control the amount of retrograde flow. For example, diminishing the amount of left-to-right shunt increases the pressure in the coronary sinus while directing more blood flow through the side limb. Some amount of blood flow into the right atrium, however, is necessary to prevent excessive pressure build-up in the coronary sinus. Preferably, the sizes of the three passageways work together to prevent the coronary sinus pressure from rising above a suitable level, e.g., of about 50 mm Hg or in the alternative of about half systemic pressure, while at the same time avoiding excessive left-to-right shunting.

The present invention also contemplates a percutaneous method of delivery of the bifurcated stent of the present invention to allow blood flow from the left ventricle to the coronary sinus.

DETAILED DESCRIPTION

Figure 1A:
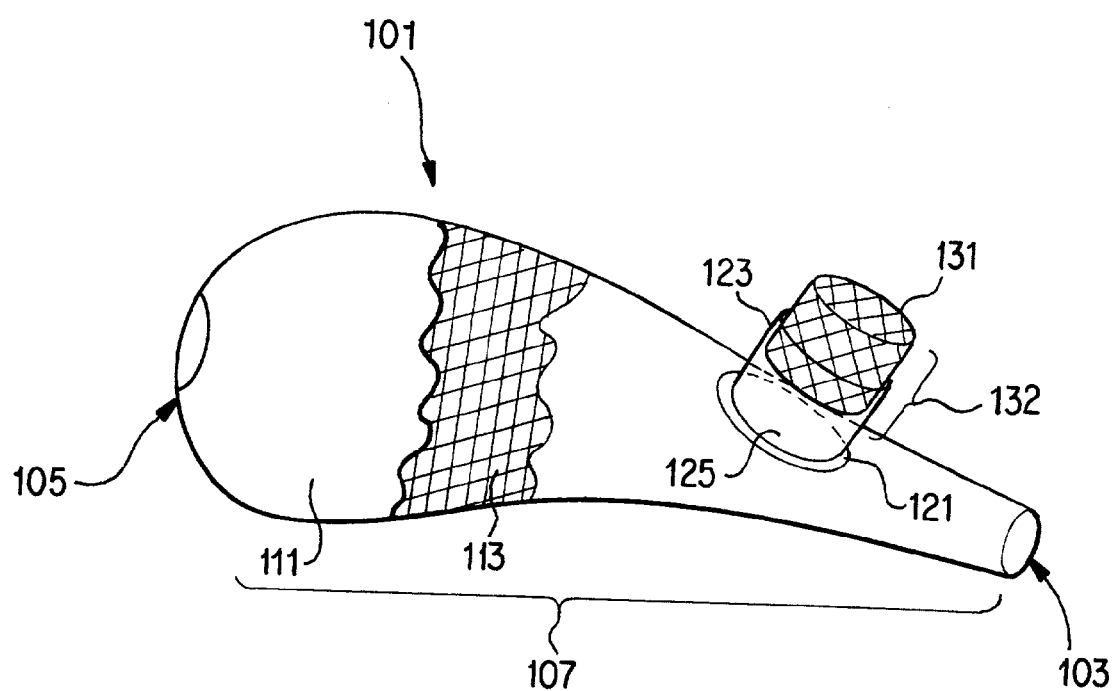
FIG. 1A shows a preferred embodiment of a bifurcated stent according to the present invention, wherein the side stent is not attached to the main stent.

A preferred embodiment of a bifurcated stent 101 according to the present invention is illustrated in FIG. 1A. The bifurcated stent 101 generally has a main covered stent 107 and a side limb 132. The main covered stent 107 generally has a tubular shape with a passageway therethrough, having a leading end 103 and a trailing end 105. The main covered stent 107 may have a slight bend or may otherwise be straight along its extent.

The main covered stent 107 generally refers to a combination of an underlying main stent 113 (bare stent) and a graft 111 (covering). The graft 111 is preferably inside the main stent 113, but may also be outside the main stent 113. In another embodiment, the stent 113 may be sandwiched between an outer graft and an inner graft (not pictured). The graft 111 is made from any of a number of commercially available materials such as PET, PTFE, or other suitable material as known in the art. Hereinafter, the combination of the graft 111 and the main stent 113 will be referred to as the main covered stent 107.

The bifurcated stent 101 also has a side limb 132, which forms the short limb of the Y or T shaped stent. The side limb 132 includes a side stent 131 and an optional cuff 123. The cuff 123, when present, is attached to the graft 111 of the main covered stent 107. The side stent 131, which is always present, however, may or may not be attached to the main stent 113 of the main covered stent 107. The side stent 131 may be attached to the main stent 113 by stitching or weaving. In an alternative embodiment, the side sent may also be attached by being a continuous weave of the main stent. Various preferred embodiments are shown in FIGS. 1A, 1B, and 1C.

In the embodiment shown in FIG. 1A, the side limb 132 includes both the cuff 123 and the side stent 131. Although the cuff 123 is pre-attached to the graft 111, the side stent 131 is not attached to the main stent 113 of the main covered stent 107. In this embodiment, the main covered stent 107 is first delivered to fit substantially within the coronary sinus, with the opening 125 facing the upstream portion of the coronary sinus. After delivering the main covered stent 107, the side stent 131 is delivered to fit within the cuff 123. The side stent 131 may also optionally fit within the opening 125.

Figure 1B:
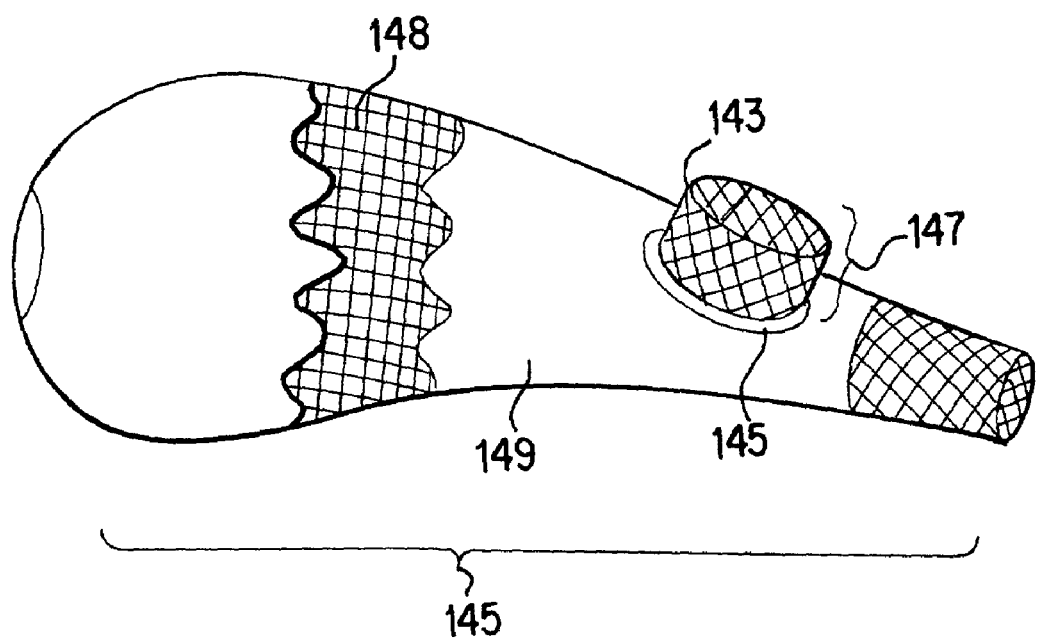
FIG. 1B shows a preferred embodiment of a bifurcated stent according to the present invention, wherein the side stent is attached to the main stent and the cuff is not present in the side limb.

In the embodiment shown in FIG. 1B, the side limb 147 includes the side stent 143 but does not contain a cuff. In further contrast to the embodiment in FIG. 1A, the side stent 143 is attached to the main stent 148, e.g., by being connected or stitched or by being a continuous weave with the main stent 148. The side stent 143 is preferably pre-attached, but may optionally be attached after delivery. The side stent 143 in this embodiment is relatively short and ranges in length from about 0.25 cm to about 1.0 cm. In this embodiment, the main covered stent 145 and the side limb 147 are delivered simultaneously since they are attached to form a single unit. The side limb 147 is preferably delivered to face the retrograde portion of the coronary sinus. In the embodiment shown in FIG. 1B, the portion of the main stent 148 near the leading end, preferably about 0.5 cm in length, is not covered with the graft 149.

Figure 1C:
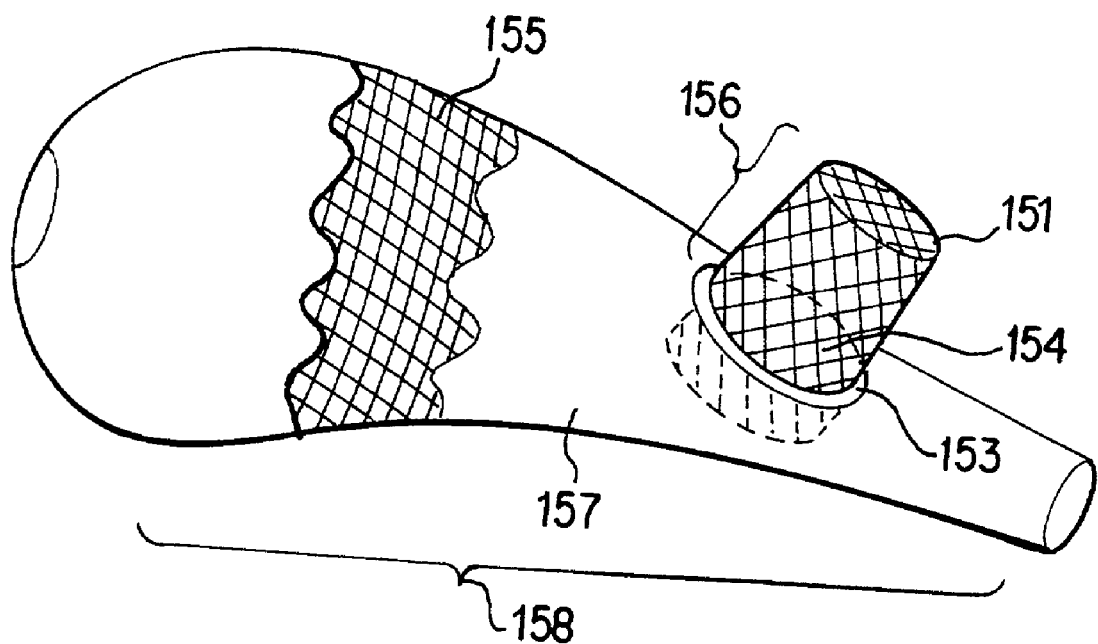
FIG. 1C shows a preferred embodiment of a bifurcated stent according to the present invention, wherein the side stent is not attached to the main stent and the cuff is not present in the side limb.

In the embodiment shown in FIG. 1C, the side limb 156 includes only the side stent 151. There is no cuff in this embodiment. Furthermore, the side limb 156 is not attached to the main stent 155 of the main covered stent 158. In this embodiment, the main covered stent 158 is first delivered with the opening 154 facing the upstream portion of the coronary sinus. Because there is no cuff as in FIG. 1A, the side stent 151 is then positioned to fit within the opening 154. In FIGS. 1A–1C, the side limbs are in contact with the main covered stent about said opening. Other embodiments and variations, not specifically disclosed but obvious to one of ordinary skill in the art, are also contemplated in the present invention. Thus, FIGS. 1A–1C as preferred embodiments are not meant to be exhaustive or limiting.

Referring back to FIG. 1A, the opening 125 is preferably circular in shape and is located in the main covered stent 107 about the mid portion along its length. (The length between the leading end 103 and the opening 125 is preferably chosen to represent the distance between the left ventricle and the coronary sinus.) The opening 125 is preferably lined with a ring 121, which is preferably made of radio-opaque material, such as platinum or gold, to facilitate placement during percutaneous delivery.

Referring to the side limb 132, the cuff 123 is made of the similar material as the graft 111 discussed above. In a preferred embodiment, the cuff 123 has a constant cross-sectional diameter equal to that of the opening 125. In another embodiment, the cross-sectional diameter of the cuff 123 varies along its length.

For the main covered stent, 107, the cross-sectional diameter varies along its length. The main covered stent 107 generally has the smallest cross-sectional diameters (or passageway) at the trailing end 105 and at the leading end 103. Thus, traveling from the trailing end 105 to the leading end 103, the cross-sectional diameter of the main covered stent 107 increases until it reaches a maximum diameter. The maximum diameter may continue, may thereafter increase or decrease, but will eventually decrease down toward the leading end 103. In a preferred embodiment as shown in FIG. 1, the main covered stent 107 has a shape that tapers in cross-sectional diameter toward the trailing end 105 and toward the leading end 103.

Referring to preferred dimensions, the length of the main covered stent 107 from the trailing end 105 to the leading end 103 is preferably from about 2 cm to about 6 cm, and more preferably from about 2 cm to about 5 cm. More particularly, the length of the main covered stent 107 from the trailing end 105 to the opening 125 is preferably from about 1 cm to about 4 cm, and more preferably about 2 cm. The length of the main covered stent 107 from the leading end 103 to the opening 125 is preferably from about 0.5 cm to about 3 cm in length, and more preferably about 1 cm.

As for the preferred diameter of the cross-sectional area (or passageway), the trailing end 105 has a diameter of from about 1 mm to about 6 mm, and more preferably from about 2 mm to about 5 mm. The diameter of the passageway at the leading end 103 is preferably from about 1 mm to about 6 mm, and more preferably from about 2 mm to about 5 mm. The opening 125 also has a cross-sectional diameter of from about 1 mm to about 6 mm, and more preferably from about 2 mm to about 5 mm. The cross-sectional diameter of the side limb 132 may either be constant or may vary along its length. In the embodiment shown in FIG. 1A, the cross-sectional diameter of the side limb 132 is approximately the same as the cross-sectional diameter of the opening 125.

As discussed above, the side limb 132 may include a side stent 131, which may or may not be attached to the main stent 113. For example, as shown in FIG. 1B, if the side stent 143 is attached (by being connected, e.g., stitched to, or by being a continuous weave with) the main stent 148, both the side limb 147 and the main covered stent 145 are allowed to expand after delivery. The side limb 147 is positioned to point toward the retrograde portion of the coronary sinus. In a preferred embodiment, the attached side stent 143 is from about 0.25 cm to about 1.0 cm in length. As shown in FIGS. 1A and 1C, however, the side stent 131 or 151, which is not attached to the main stent 113 or 155, is preferably from about 0.5 cm to about 2 cm in length.

Referring back to FIG. 1A as an example, the side stent 131 is made preferably of surgical grade stainless steel or nitinol in woven design, and may be of any other configuration or material as known in the art or as commercially available. The side stent 131 also has a tubular shape with a passageway therethrough. The side stent 131 has a cross-sectional diameter after expansion of preferably from about 1 mm to about 6 mm, and more preferably from about 2 mm to about 5 mm.

Although the cuff 123 is optional, it is advantageous in that it allows for a greater margin of error in inserting the side stent 131 into the retrograde portion of the coronary sinus. The cuff 123 allows the side stent 131 to be inserted in a more forgiving manner should the opening 125 not be aligned perfectly with the retrograde portion of the coronary sinus. In an alternative embodiment, the side stent 131 may protrude through opening 125 as a bare stent without the cuff 123.

The main stent 113 and side stent 131 are preferably made of a flexible material that can withstand bending without kinking to allow fluid passageway therethrough. The main stent 113 and side stent 131 also allow compression and expansion cross-sectionally. A number of suitable commercially available stents with these desired characteristics may be employed in practicing the present invention. Metallic stents as well as non-metallic stents may be used in the construction. Non-metallic stents, for example, may be made of a suitable plastic material. Suitable designs include various wire mesh designs and weave configurations as known in the art. In one embodiment, the main stent 113 and side stent 131 may have a coiled construction as known in the art.

Figure 2:
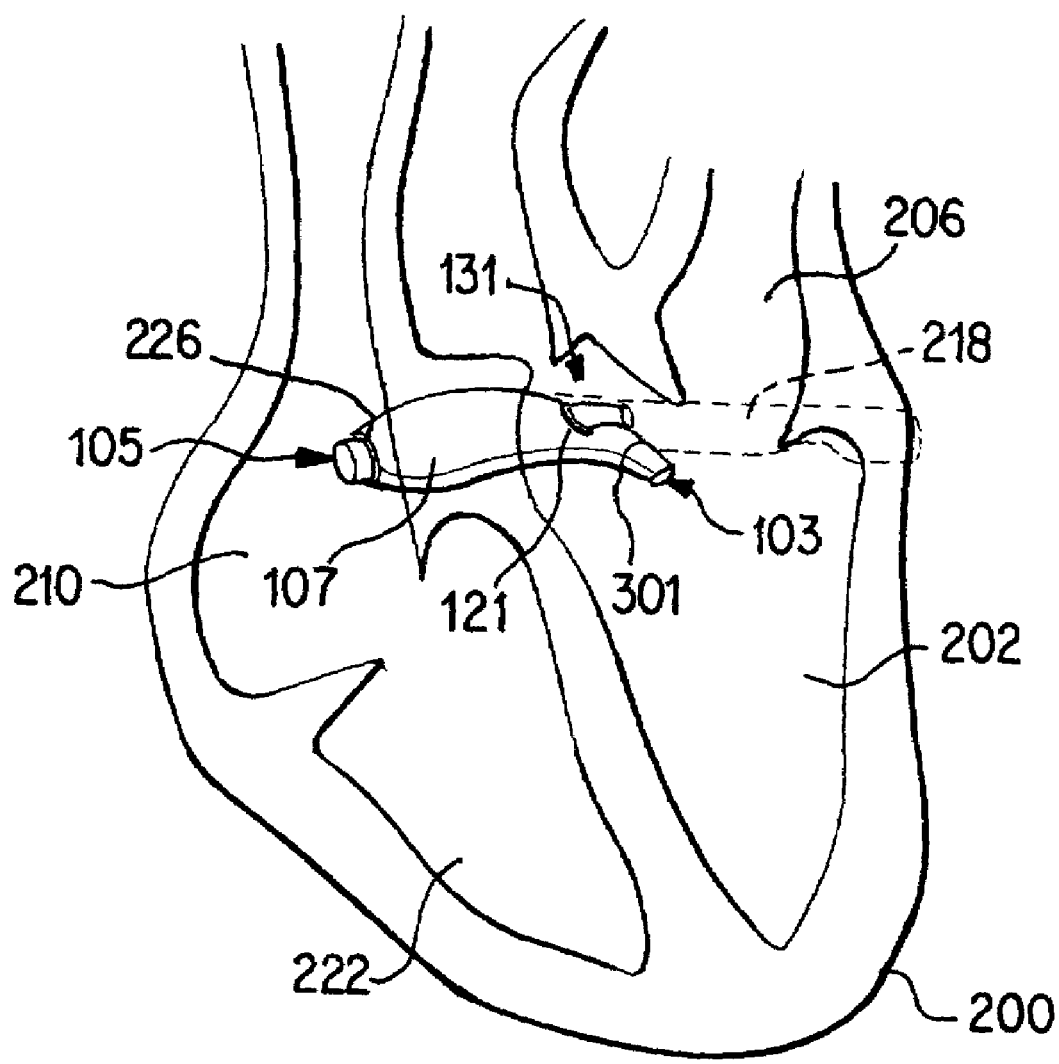
FIG. 2 represents a preferred placement of the bifurcated stent according to the present invention in a schematic diagram of the heart.

Referring now to FIG. 2, the bifurcated stent 101 of FIG. 1 is positioned in a schematic diagram of the human heart 200. The heart 200 generally has a left ventricle 202, a left atrium 206, a right ventricle 222, and a right atrium 210. The left ventricle 202 is primarily responsible for delivering oxygenated blood to the body. The left atrium 206 receives oxygenated blood from the lungs, which is then delivered to the left ventricle 202. The right atrium 210 is primarily responsible for receiving deoxygenated blood from the body. Deoxygenated blood then flows into the right ventricle 222 before being sent to the lungs for oxygenation. After perfusing the heart, blood from the coronary arteries normally drains to the coronary sinus 218 and into the right atrium 210. The coronary ostium 226 connects the right atrium 210 to the coronary sinus 218.

Figure 3:
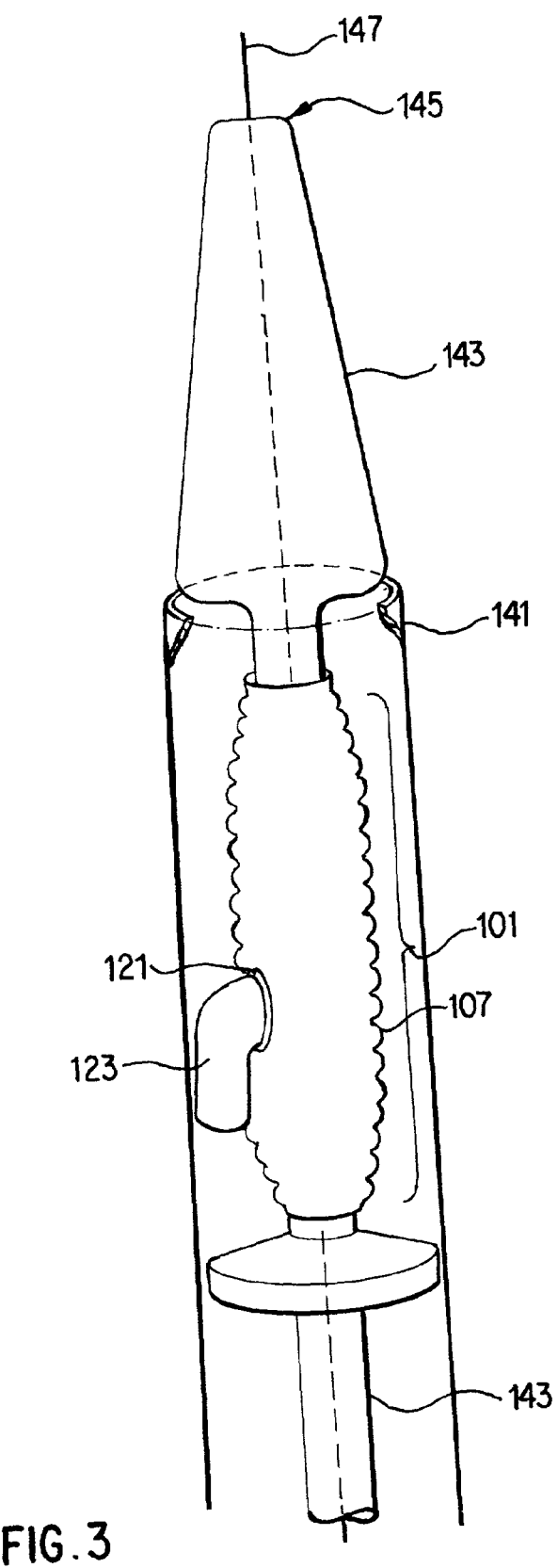
FIG. 3 shows an apparatus for percutaneously delivering the bifurcated stent of the present invention.

In a preferred embodiment as shown in FIG. 3, the bifurcated stent 102, which is compressed onto a catheter 143 and covered by a retractable sheath 141, is introduced and placed into position before removing the sheath to expose the bifurcated stent 101. The method used by Patel et al. may be employed in delivering the stent according to present invention. Patel et al., *Percutaneous Transmyocardial Intracardiac Retroperfusion Shunts: Technical Feasibility In a Canine Model,* JVIR 2000, 11:382–390. Patel, et al. modifies the stent delivery method as described by Rosch, et al. in Rosch, et al., *Coaxial Catheter, Needle System for Transjugular Portal Vein Entrance,* JVIR, Vol. 4, No. 1, pp. 145–147, 1993.

Referring back to FIG. 2, a sheath is introduced into the jugular vein percutaneously, through which the coronary sinus 218 is catheterized and a wire is introduced. Once the catheter is removed, a stiff needle guide combination is passed over the wire as known in the art. The needle guide is aimed at the left ventricle 202 (marked with a percutaneously introduced pigtail catheter) and pierced through the coronary sinus wall into the left ventricle 202. A guide wire is passed into the aorta (not pictured) and the needle guide is removed to leave a hole 301. The hole 301 may be widened with a balloon catheter. The hole punctured allows for the main covered stent 107 to fit therebetween, and therefore blood flows from the left ventricle 202 into the passageway of the main covered stent 107.

Delivery involves placing the bifurcated stent 101 within a retractable sheath 141 as seen in FIG. 3 around catheter 143. Catheter 143 also has a tip 145 which is guided by the guide wire 147. After positioning, the retractable sheath 141 of the catheter 143 is removed, and the bifurcated stent 101 is allowed to expand, if the stent 101 is a self-expanding stent.

Before removing the retractable sheath 141, however, the catheter 143 is preferably rotated about the guide wire 147 to align the opening or the ring 121 with the upstream portion of the coronary sinus 218. A catheter placed in the coronary sinus 218 for contrast injection may aid in aligning the ring 121 with the coronary sinus 218. Referring back to FIG. 1, the opening 125 is bordered by the ring 121, and the ring 121 is made of radio-opaque material, such as platinum or gold, to aide in the alignment of the opening 125 with the coronary sinus 218. Thus, under fluoroscopic control, the ring 121 is aligned with the opaque or marked element in the upstream portion of the coronary sinus 218. By occluding the trailing end 105 of the main covered stent 107 with a balloon catheter, blood flow will open the cuff 123 into the upstream portion of the coronary sinus 218 for alignment with the coronary sinus 218. The cuff 123 is then reinforced with a side stent 131, if the side stent 131 is not already attached to the main stent 113.

During delivery, the opening 125 or the side limb 132 is preferably aligned with the retrograde portion of the coronary sinus 218 as accurately as possible. After the opening 125 is aligned with the coronary sinus 218, however, an additional extension stent (not pictured) as known in the art may be coupled to the main covered stent 107 at the leading end 103 so that the leading end 103 will be located within the left ventricle 202.

Once the ring 125 is aligned with the coronary sinus, the retractable sheath 141 is pulled back, and the bifurcated stent 101 is allowed to expand. The main covered stent 113 (see FIG. 1) and/or the side stent 131 is preferably self expanding, which expands upon introduction into the body. If the stent is not self expanding or has not fully expanded, a balloon catheter as known in the art may be used to expand the main covered stent 107 of the invention.

Referring again to FIG. 2, the leading end 103 is positioned preferably within the left ventricle 202. If the leading end 103 is not in the left ventricle 202, an additional extension stent (not pictured), as discussed above, may be used to further elongate the leading end 103 portion of the stent 113. The main covered stent 107 is positioned to lie primarily within the coronary sinus 218. The trailing end 105 is preferably placed within the right atrium 210. If the main covered stent 107 is too short for the trailing end 105 to reach the right atrium 210, an extension (not pictured) as known in the art may be used. Alternatively, the main covered stent 107 may be within the coronary sinus 218, preferably near the coronary ostium 226. To help gauge the approximate length of the main covered stent 107, a guide wire with radio-opaque marking every 1 cm may be used to measure the various relevant distances between the left ventricle 202 and the coronary ostium 226. In another embodiment, the trailing end 105 may be positioned within the coronary sinus 218.

As the main covered stent 107 expands after release from the retractable sheath 141, it expands to form a friction fit within the inner wall of the coronary sinus 218. This friction fit keeps the main covered stent 107 stationary to prevent axial rotation and migration and therefore keeps the ring 121 or the side limb 132 in alignment with the retrograde portion of the coronary sinus 218. The graft 111 of the main covered stent 107 directs blood flowing into the coronary sinus to flow through the passageway at the trailing end 105 or through the passageway of the side limb 132. Some amount of blood in the main covered stent may also flow into the left ventricle through the leading end 103.

The amount of blood flow through the side limb 132 is generally inversely related to the amount of left-to-right shunting. Blood flowing from the left ventricle 202 into the main covered stent 107 flows out through the opening 125 and the side limb 132 to provide retrograde perfusion to the myocardium. The size of the diameter of the passageway at the trailing end 105 influences the amount of shunt. For example, decreasing the size of the passageway at the trailing end 105 increases the retrograde perfusion of the myocardium. If the flow rate to the passageway at the trailing end 105 is too great, the heart tissue would not adequately be perfused. Too small a diameter, however, may increase the pressure within the coronary sinus 218 to dangerous levels. Thus, the passageway at the trailing end 105 should be large enough to prevent excess pressure build-up, but at the same time be restrictive enough to allow the heart to be supplied with oxygenated blood. The size of the three passageways, at the leading end 103, the trailing end 105, and the opening 125, are interrelated and balanced to influence the left-to-right shunt and the coronary sinus pressure. As an illustrative example only, and not as a limitation, the amount of shunting may preferably be less than approximately a one-and-a-half to one shunt ratio. In a preferred embodiment, the pressure within the coronary sinus 218 does not exceed about 50 mm Hg. In an alternative embodiment, the pressure within the coronary sinus 218 does not exceed about half systemic pressure.

Coronary sinus pressure may also be controlled by the amount of blood flowing from the left ventricle 202 into the main covered stent 107. Thus, the size of the passageway at the leading end 103 may be chosen in relation to the size of the passageway at the trailing end 105 to provide efficient retrograde perfusion of heart tissue without excessive pressure build-up.

Figure 4:
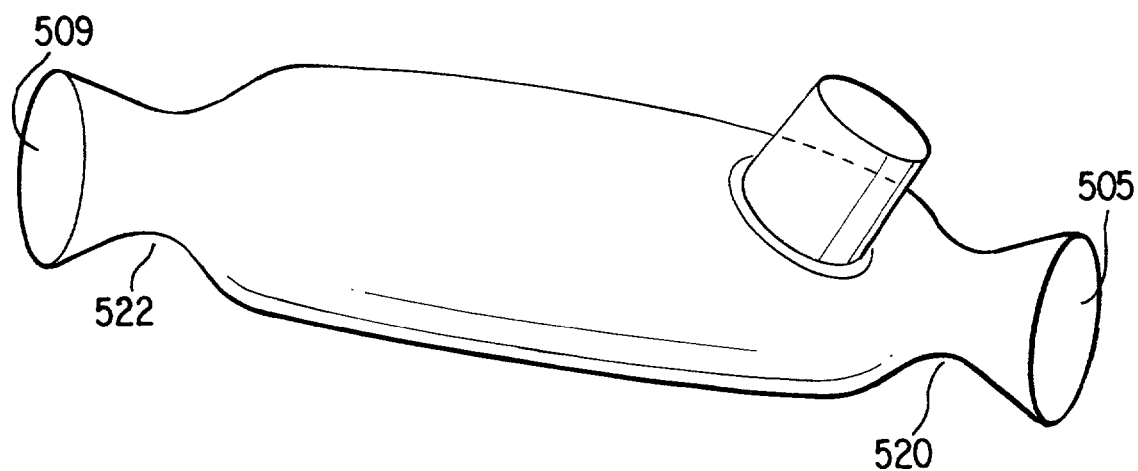
FIG. 4 shows an alternative embodiment of a bifurcated stent having flaring ends with constrictions near the trailing end and the leading end.

In an alternative embodiment, as seen in FIG. 4, the smallest cross-sectional diameter of the stent 501 may not be at the leading end 505 and the trailing end 509, but may be approximately 1 mm to about 1 cm from the leading end 505 and the trailing end 509. Thus, the stent 101 would have one or two flaring ends. The smallest cross-sectional area would be at constriction 520, which is near the leading end 505, and at constriction 522, which is near the trailing end 509. The cross-sectional area from the constriction 520 to the leading end 505 or the trailing end 509 may also be constant.

I claim:

1. A bifurcated stent comprising:
   a main covered stent having a main stent covered by a graft and defining an opening, and having a leading end and a trailing end, wherein the main covered stent tapers in cross-sectional diameter toward the trailing end and the leading end; and
   a side limb having a side stent, wherein side limb is in contact with said main covered stent about said opening.

2. The bifurcated stent according to claim 1, wherein said side stent is not attached to said main stent of said main covered stent.

3. The bifurcated stent according to claim 1, wherein said limb further has a cuff that is attached to said graft of said main covered stent.

4. The bifurcated stent according to claim 3, wherein said cuff is attached by being connected to said graft.

5. The bifurcated stent according to claim 3, wherein said cuff is attached by being continuous with said graft.

6. The bifurcated stent according to claim 3, wherein said side stent is not attached to said main stent of said main covered stent.

7. The bifurcated stent according to claim 1, wherein said stent is attached to said main stent of said main covered stent.

8. The bifurcated stent according to claim 7, wherein said side stent is attached by being connected to said main stent.

9. The bifurcated stent according to claim 7, wherein said side stent is attached by being continuous with said main stent.

10. The bifurcated stent according to claim 1, wherein said cross-sectional diameter of said main covered stent varies along its extent.

11. The bifurcated stent according to claim 1, wherein a portion of said main covered stent has a constant cross section.

12. The bifurcated stent according to claim 1, wherein said side limb and said opening have similar cross section.

13. The bifurcated stent according to claim 1, wherein a cross section of said leading end is appropriately sized to control blood flow from said left ventricle into said main covered stent.

14. The bifurcated stent according to claim 1, wherein a cross section of said trailing end is appropriately sized to control blood flow into a right atrium.

15. The bifurcated stent according to claim 1, wherein cross section of said opening and said side limb are appropriately sized to control the amount of blood flowing into the retrograde portion of the coronary sinus.

16. The bifurcated stent according to claim 1, wherein cross section of said trailing end, said leading end, said opening, and said side limb are appropriately sized to prevent pressure level within said coronary sinus from rising above about 50 mm Hg.

17. The bifurcated stent according to claim 1, wherein cross section of said trailing end, said leading end, said opening, and said side limb are appropriately sized to prevent pressure level within the coronary sinus from rising above about half systemic pressure.

18. The bifurcated stent according to claim 1, wherein said trailing end, said leading end, said opening, and said side limb are each from about 1 mm to about 6 mm in diameter.

19. The bifurcated stent according to claim 18, wherein said trailing end, said leading end, said opening, and said side limb are each from about 2 mm to about 5 mm in diameter.

20. The bifurcated stent according to claim 1, wherein said side limb and said opening have similar cross section.

21. The bifurcated stent according to claim 1, wherein cross section of said side limb varies along its extent.

22. The bifurcated stent according to claim 1, wherein said side limb is from about 1 mm to about 6 mm in diameter.

23. The bifurcated stent according to claim 1, wherein said main covered stent and said side limb allow compression and expansion.

24. The bifurcated stent according to claim 1, wherein said main covered stent and said side limb are flexible.

25. The bifurcated stent according to claim 1, wherein said main covered stent and said side stent are of mesh construction.

26. The bifurcated stent according to claim 1, wherein said main covered stent and said side stent are of coiled construction.

27. The bifurcated stent according to claim 1, wherein said main covered stent does not exceed from about 6 mm to about 12 mm in diameter.

28. The bifurcated stent according to claim 1, wherein said graft is inside said main stent.

29. The bifurcated stent according to claim 1, wherein said graft is outside said main stent.

30. The bifurcated stent according to claim 1, wherein said main stent is sandwiched between an inside graft and an outside graft.

31. The bifurcated stent according to claim 1, wherein said main covered stent expands and forms a friction fit.

32. The bifurcated stent according to claim 1, wherein a portion of said main stent near said trailing end is not covered by said graft.

33. A bifurcated stent for facilitating retrograde supply of oxygenated blood to heart tissue through a coronary sinus comprising:

a main covered stent having a main stent covered by a graft and defining an opening, and having a leading end and a trailing end, wherein said main covered stent tapers in cross sectional area toward said leading end and toward said trailing end, and a side limb comprising a side stent, wherein said side limb is in contact with said main covered stent about said opening.

34. The bifurcated stent according to claim 1, wherein said leading end is configured to be positioned in a left ventricle and said trailing end is configured to be positioned in a right atrium.

35. A bifurcated stent comprising:

a main covered stent having a main stent covered by a graft and defining an opening, and having a leading end and a trailing end, wherein said main covered stent exhibits a constriction near said leading end and a constriction near said trailing end; and a side limb having a side stent, wherein side limb is in contact with said main covered stent about said opening.

36. The bifurcated stent according to claim 35, wherein said side stent is not attached to said main stent of said main covered stent.

37. The bifurcated stent according to claim 35, wherein said limb further has a cuff that is attached to said graft of said main covered stent.

38. The bifurcated stent according to claim 37, wherein said cuff is attached by being connected to said graft.

39. The bifurcated stent according to claim 37, wherein said cuff is attached by being continuous with said graft.

40. The bifurcated stent according to claim 37, wherein said side stent is not attached to said main stent of said main covered stent.

41. The bifurcated stent according to claim 35, wherein said stent is attached to said main stent of said main covered stent.

42. The bifurcated stent according to claim 41, wherein said side stent is attached by being connected to said main stent.

43. The bifurcated stent according to claim 41, wherein said side stent is attached by being continuous with said main stent.

44. The bifurcated stent according to claim 35, wherein a portion of said main covered stent has a constant cross section.

45. The bifurcated stent according to claim 35, wherein said side limb and said opening have similar cross section.

46. The bifurcated stent according to claim 35, wherein a cross section of said leading end is appropriately sized to control blood flow from said left ventricle into said main covered stent.

47. The bifurcated stent according to claim 35, wherein a cross section of said trailing end is appropriately sized to control blood flow into a right atrium.

48. The bifurcated stent according to claim 35, wherein cross section of said opening and said side limb are appropriately sized to control the amount of blood flowing into the retrograde portion of the coronary sinus.

49. The bifurcated stent according to claim 35, wherein cross section of said trailing end, said leading end, said opening, and said side limb are appropriately sized to prevent pressure level within said coronary sinus from rising above about 50 mm Hg.

50. The bifurcated stent according to claim 35, wherein cross section of said trailing end, said leading end, said opening, and said side limb are appropriately sized to prevent pressure level within the coronary sinus from rising above about half systemic pressure.

51. The bifurcated stent according to claim 35, wherein said trailing end, said leading end, said opening, and said side limb are each from about 1 mm to about 6 mm in diameter.

52. The bifurcated stent according to claim 35, wherein said trailing end, said leading end, said opening, and said side limb are each from about 2 mm to about 5 mm in diameter.

53. The bifurcated stent according to claim 35, wherein said side limb and said opening have similar cross section.

54. The bifurcated stent according to claim 35, wherein cross section of said side limb varies along its extent.

55. The bifurcated stent according to claim 35, wherein said side limb is from about 1 mm to about 6 mm in diameter.

56. The bifurcated stent according to claim 35, wherein said main covered stent and said side limb allow compression and expansion.

57. The bifurcated stent according to claim 35, wherein said main covered stent and said side limb are flexible.

58. The bifurcated stent according to claim 35, wherein said main covered stent and said side stent are of mesh construction.

59. The bifurcated stent according to claim 35, wherein said main covered stent and said side stent are of coiled construction.

60. The bifurcated stent according to claim 35, wherein said main covered stent does not exceed from about 6 mm to about 12 mm in diameter.

61. The bifurcated stent according to claim 35, wherein said graft is inside said main stent.

62. The bifurcated stent according to claim 35, wherein said graft is outside said main stent.

63. The bifurcated stent according to claim 35, wherein said main stent is sandwiched between an inside graft and an outside graft.

64. The bifurcated stent according to claim 35, wherein said main covered stent expands and forms a friction fit.

65. The bifurcated stent according to claim 35, wherein a portion of said main stent near said trailing end is not covered by said graft.

66. A method for facilitating retrograde supply of oxygenated blood from a left ventricle to heart tissue via a coronary sinus comprising puncturing a hole through said coronary sinus and a wall of said left ventricle and delivering the bifurcated stent of claim 1.

67. A method for facilitating retrograde supply of oxygenated blood from a left ventricle to heart tissue via a coronary sinus comprising puncturing a hole through said coronary sinus and a wall of said left ventricle and delivering the bifurcated stent of claim 2.

68. A method for facilitating retrograde supply of oxygenated blood from a left ventricle to heart tissue via a coronary sinus comprising puncturing a hole through said coronary sinus and a wall of said left ventricle and delivering the bifurcated stent of claim 3.

69. A method for facilitating retrograde supply of oxygenated blood from a left ventricle to heart tissue via a coronary sinus comprising puncturing a hole through said coronary sinus and a wall of said left ventricle and delivering the bifurcated stent of claim 4.

70. A method for facilitating retrograde supply of oxygenated blood from a left ventricle to heart tissue via a coronary sinus comprising puncturing a hole through said coronary sinus and a wall of said left ventricle and delivering the bifurcated stent of claim 5.

71. A method for facilitating retrograde supply of oxygenated blood from a left ventricle to heart tissue via a coronary sinus comprising puncturing a hole through said coronary sinus and a wall of said left ventricle and delivering the bifurcated stent of claim 6.

72. A method for facilitating retrograde supply of oxygenated blood from a left ventricle to heart tissue via a coronary sinus comprising puncturing a hole through said coronary sinus and a wall of said left ventricle and delivering the bifurcated stent of claim 7.

73. A method for facilitating retrograde supply of oxygenated blood from a left ventricle to heart tissue via a coronary sinus comprising puncturing a hole through said coronary sinus and a wall of said left ventricle and delivering the bifurcated stent of claim 8.

74. A method for facilitating retrograde supply of oxygenated blood from a left ventricle to heart tissue via a coronary sinus comprising puncturing a hole through said coronary sinus and a wall of said left ventricle and delivering the bifurcated stent of claim 9.

75. A method for facilitating retrograde supply of oxygenated blood from a left ventricle to heart tissue via a coronary sinus comprising puncturing a hole through said coronary sinus and a wall of said left ventricle and delivering the bifurcated stent of claim 10.

76. A method for facilitating retrograde supply of oxygenated blood from a left ventricle to heart tissue via a coronary sinus comprising puncturing a hole through said coronary sinus and a wall of said left ventricle and delivering the bifurcated stent of claim 11.

77. A method for facilitating retrograde supply of oxygenated blood from a left ventricle to heart tissue via a coronary sinus comprising puncturing a hole through said coronary sinus and a wall of said left ventricle and delivering the bifurcated stent of claim 12.

78. A method for facilitating retrograde supply of oxygenated blood from a left ventricle to heart tissue via a coronary sinus comprising puncturing a hole through said coronary sinus and a wall of said left ventricle and delivering the bifurcated stent of claim 13.

79. A method for facilitating retrograde supply of oxygenated blood from a left ventricle to heart tissue via a coronary sinus comprising puncturing a hole through said coronary sinus and a wall of said left ventricle and delivering the bifurcated stent of claim 14.

80. A method for facilitating retrograde supply of oxygenated blood from a left ventricle to heart tissue via a coronary sinus comprising puncturing a hole through said coronary sinus and a wall of said left ventricle and delivering the bifurcated stent of claim 15.

81. A method for facilitating retrograde supply of oxygenated blood from a left ventricle to heart tissue via a coronary sinus comprising puncturing a hole through said coronary sinus and a wall of said left ventricle and delivering the bifurcated stent of claim 16.

82. A method for facilitating retrograde supply of oxygenated blood from a left ventricle to heart tissue via a coronary sinus comprising puncturing a hole through said coronary sinus and a wall of said left ventricle and delivering the bifurcated stent of claim 17.

83. A method for facilitating retrograde supply of oxygenated blood from a left ventricle to heart tissue via a coronary sinus comprising puncturing a hole through said coronary sinus and a wall of said left ventricle and delivering the bifurcated stent of claim 18.

84. A method for facilitating retrograde supply of oxygenated blood from a left ventricle to heart tissue via a coronary sinus comprising puncturing a hole through said coronary sinus and a wall of said left ventricle and delivering the bifurcated stent of claim 19.

85. A method for facilitating retrograde supply of oxygenated blood from a left ventricle to heart tissue via a coronary sinus comprising puncturing a hole through said coronary sinus and a wall of said left ventricle and delivering the bifurcated stent of claim 20.

86. A method for facilitating retrograde supply of oxygenated blood from a left ventricle to heart tissue via a coronary sinus comprising puncturing a hole through said coronary sinus and a wall of said left ventricle and delivering the bifurcated stent of claim 21.

87. A method for facilitating retrograde supply of oxygenated blood from a left ventricle to heart tissue via a coronary sinus comprising puncturing a hole through said coronary sinus and a wall of said left ventricle and delivering the bifurcated stent of claim 22.

88. A method for facilitating retrograde supply of oxygenated blood from a left ventricle to heart tissue via a coronary sinus comprising puncturing a hole through said coronary sinus and a wall of said left ventricle and delivering the bifurcated stent of claim 23.

89. A method for facilitating retrograde supply of oxygenated blood from a left ventricle to heart tissue via a coronary sinus comprising puncturing a hole through said coronary sinus and a wall of said left ventricle and delivering the bifurcated stent of claim 24.

90. A method for facilitating retrograde supply of oxygenated blood from a left ventricle to heart tissue via a coronary sinus comprising puncturing a hole through said coronary sinus and a wall of said left ventricle and delivering the bifurcated stent of claim 25.

91. A method for facilitating retrograde supply of oxygenated blood from a left ventricle to heart tissue via a coronary sinus comprising puncturing a hole through said coronary sinus and a wall of said left ventricle and delivering the bifurcated stent of claim 26.

92. A method for facilitating retrograde supply of oxygenated blood from a left ventricle to heart tissue via a coronary sinus comprising puncturing a hole through said coronary sinus and a wall of said left ventricle and delivering the bifurcated stent of claim 27.

93. A method for facilitating retrograde supply of oxygenated blood from a left ventricle to heart tissue via a coronary sinus comprising puncturing a hole through said coronary sinus and a wall of said left ventricle and delivering the bifurcated stent of claim 28.

94. A method for facilitating retrograde supply of oxygenated blood from a left ventricle to heart tissue via a coronary sinus comprising puncturing a hole through said coronary sinus and a wall of said left ventricle and delivering the bifurcated stent of claim 29.

95. A method for facilitating retrograde supply of oxygenated blood from a left ventricle to heart tissue via a coronary sinus comprising puncturing a hole through said coronary sinus and a wall of said left ventricle and delivering the bifurcated stent of claim 30.

96. A method for facilitating retrograde supply of oxygenated blood from a left ventricle to heart tissue via a coronary sinus comprising puncturing a hole through said coronary sinus and a wall of said left ventricle and delivering the bifurcated stent of claim 31.

97. A method for facilitating retrograde supply of oxygenated blood from a left ventricle to heart tissue via a coronary sinus comprising puncturing a hole through said coronary sinus and a wall of said left ventricle and delivering the bifurcated stent of claim 32.

98. A method for facilitating retrograde supply of oxygenated blood from a left ventricle to heart tissue via a coronary sinus comprising puncturing a hole through said coronary sinus and a wall of said left ventricle and delivering the bifurcated stent of claim 34.

99. A method for facilitating retrograde supply of oxygenated blood from a left ventricle to heart tissue via a coronary sinus comprising puncturing a hole through said coronary sinus and a wall of said left ventricle and delivering the bifurcated stent of claim 35.

100. A method for facilitating retrograde supply of oxygenated blood from a left ventricle to heart tissue via a coronary sinus comprising puncturing a hole through said coronary sinus and a wall of said left ventricle and delivering the bifurcated stent of claim 36.

101. A method for facilitating retrograde supply of oxygenated blood from a left ventricle to heart tissue via a coronary sinus comprising puncturing a hole through said coronary sinus and a wall of said left ventricle and delivering the bifurcated stent of claim 37.

102. A method for facilitating retrograde supply of oxygenated blood from a left ventricle to heart tissue via a coronary sinus comprising puncturing a hole through said coronary sinus and a wall of said left ventricle and delivering the bifurcated stent of claim 38.

103. A method for facilitating retrograde supply of oxygenated blood from a left ventricle to heart tissue via a coronary sinus comprising puncturing a hole through said coronary sinus and a wall of said left ventricle and delivering the bifurcated stent of claim 39.

104. A method for facilitating retrograde supply of oxygenated blood from a left ventricle to heart tissue via a coronary sinus comprising puncturing a hole through said coronary sinus and a wall of said left ventricle and delivering the bifurcated stent of claim 40.

105. A method for facilitating retrograde supply of oxygenated blood from a left ventricle to heart tissue via a coronary sinus comprising puncturing a hole through said coronary sinus and a wall of said left ventricle and delivering the bifurcated stent of claim 41.

106. A method for facilitating retrograde supply of oxygenated blood from a left ventricle to heart tissue via a coronary sinus comprising puncturing a hole through said coronary sinus and a wall of said left ventricle and delivering the bifurcated stent of claim 42.

107. A method for facilitating retrograde supply of oxygenated blood from a left ventricle to heart tissue via a coronary sinus comprising puncturing a hole through said coronary sinus and a wall of said left ventricle and delivering the bifurcated stent of claim 43.

108. A method for facilitating retrograde supply of oxygenated blood from a left ventricle to heart tissue via a coronary sinus comprising puncturing a hole through said coronary sinus and a wall of said left ventricle and delivering the bifurcated stent of claim 44.

109. A method for facilitating retrograde supply of oxygenated blood from a left ventricle to heart tissue via a coronary sinus comprising puncturing a hole through said coronary sinus and a wall of said left ventricle and delivering the bifurcated stent of claim 45.

110. A method for facilitating retrograde supply of oxygenated blood from a left ventricle to heart tissue via a coronary sinus comprising puncturing a hole through said 111. A method for facilitating retrograde supply of oxygenated blood from a left ventricle to heart tissue via a coronary sinus comprising puncturing a hole through said coronary sinus and a wall of said left ventricle and delivering the bifurcated stent of claim 47.

112. A method for facilitating retrograde supply of oxygenated blood from a left ventricle to heart tissue via a coronary sinus comprising puncturing a hole through said coronary sinus and a wall of said left ventricle and delivering the bifurcated stent of claim 48.

113. A method for facilitating retrograde supply of oxygenated blood from a left ventricle to heart tissue via a coronary sinus comprising puncturing a hole through said coronary sinus and a wall of said left ventricle and delivering the bifurcated stent of claim 49.

114. A method for facilitating retrograde supply of oxygenated blood from a left ventricle to heart tissue via a coronary sinus comprising puncturing a hole through said coronary sinus and a wall of said left ventricle and delivering the bifurcated stent of claim 50.

115. A method for facilitating retrograde supply of oxygenated blood from a left ventricle to heart tissue via a coronary sinus comprising puncturing a hole through said coronary sinus and a wall of said left ventricle and delivering the bifurcated stent of claim 51.

116. A method for facilitating retrograde supply of oxygenated blood from a left ventricle to heart tissue via a coronary sinus comprising puncturing a hole through said coronary sinus and a wall of said left ventricle and delivering the bifurcated stent of claim 52.

117. A method for facilitating retrograde supply of oxygenated blood from a left ventricle to heart tissue via a coronary sinus comprising puncturing a hole through said coronary sinus and a wall of said left ventricle and delivering the bifurcated stent of claim 53.

118. A method for facilitating retrograde supply of oxygenated blood from a left ventricle to heart tissue via a coronary sinus comprising puncturing a hole through said coronary sinus and a wall of said left ventricle and delivering the bifurcated stent of claim 54.

119. A method for facilitating retrograde supply of oxygenated blood from a left ventricle to heart tissue via a coronary sinus comprising puncturing a hole through said coronary sinus and a wall of said left ventricle and delivering the bifurcated stent of claim 55.

120. A method for facilitating retrograde supply of oxygenated blood from a left ventricle to heart tissue via a coronary sinus comprising puncturing a hole through said coronary sinus and a wall of said left ventricle and delivering the bifurcated stent of claim 56.

121. A method for facilitating retrograde supply of oxygenated blood from a left ventricle to heart tissue via a coronary sinus comprising puncturing a hole through said coronary sinus and a wall of said left ventricle and delivering the bifurcated stent of claim 57.

122. A method for facilitating retrograde supply of oxygenated blood from a left ventricle to heart tissue via a coronary sinus comprising puncturing a hole through said coronary sinus and a wall of said left ventricle and delivering the bifurcated stent of claim 58.

123. A method for facilitating retrograde supply of oxygenated blood from a left ventricle to heart tissue via a coronary sinus comprising puncturing a hole through said coronary sinus and a wall of said left ventricle and delivering the bifurcated stent of claim 59.

124. A method for facilitating retrograde supply of oxygenated blood from a left ventricle to heart tissue via a coronary sinus comprising puncturing a hole through said coronary sinus and a wall of said left ventricle and delivering the bifurcated stent of claim 60.

125. A method for facilitating retrograde supply of oxygenated blood from a left ventricle to heart tissue via a coronary sinus comprising puncturing a hole through said coronary sinus and a wall of said left ventricle and delivering the bifurcated stent of claim 61.

126. A method for facilitating retrograde supply of oxygenated blood from a left ventricle to heart tissue via a coronary sinus comprising puncturing a hole through said coronary sinus and a wall of said left ventricle and delivering the bifurcated stent of claim 62.

127. A method for facilitating retrograde supply of oxygenated blood from a left ventricle to heart tissue via a coronary sinus comprising puncturing a hole through said coronary sinus and a wall of said left ventricle and delivering the bifurcated stent of claim 63.

128. A method for facilitating retrograde supply of oxygenated blood from a left ventricle to heart tissue via a coronary sinus comprising puncturing a hole through said coronary sinus and a wall of said left ventricle and delivering the bifurcated stent of claim 64.

129. A method for facilitating retrograde supply of oxygenated blood from a left ventricle to heart tissue via a coronary sinus comprising puncturing a hole through said coronary sinus and a wall of said left ventricle and delivering the bifurcated stent of claim 65.

\* \* \* \* \*